(12) United States Patent
Deshpande et al.

(10) Patent No.: US 6,555,680 B1
(45) Date of Patent: Apr. 29, 2003

(54) METHOD FOR THE PREPARATION OF CEFTIOFUR SODIUM

(75) Inventors: Pandurang Balwant Deshpande, Tamilnadu (IN); Pramod Narayan Deshpande, Tamilnadu (IN); Milind Ramkrishna Kulkarni, Tamilnadu (IN); Parven Kumar Luthra, Tamilnadu (IN)

(73) Assignee: Orchid Chemicals & Pharmaceuticals Ltd., Tamil Nadu (IN)

( * ) Notice: Subject to any disclaimer, the term of this patent is extended or adjusted under 35 U.S.C. 154(b) by 0 days.

(21) Appl. No.: 10/006,354

(22) Filed: Dec. 10, 2001

(51) Int. Cl.$^7$ ............................................. C07D 501/36
(52) U.S. Cl. ...................................................... 540/227
(58) Field of Search .......................................... 540/227

(56) References Cited

U.S. PATENT DOCUMENTS

| | | |
|---|---|---|
| 4,464,367 A | 8/1984 | Labeeuw et al. |
| 4,877,782 A | 10/1989 | Cazers et al. |
| 4,902,683 A | 2/1990 | Amin et al. |
| 4,937,330 A | 6/1990 | Sacks et al. |
| 2002/0028931 A1 * | 3/2002 | Dandala ..................... 540/227 |

* cited by examiner

*Primary Examiner*—Mark L. Berch
(74) *Attorney, Agent, or Firm*—Burns, Doane, Swecker & Mathis, L.L.P.

(57) ABSTRACT

The present invention relates to a process for the preparation of sodium salt of Ceftiofur as given in Formula I, directly from its amine salt using sodium base.

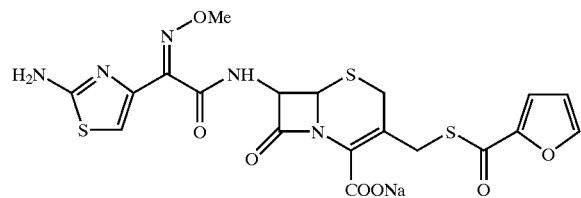

(I)

22 Claims, No Drawings

METHOD FOR THE PREPARATION OF CEFTIOFUR SODIUM

FIELD OF THE INVENTION

The present invention discloses a new process for the preparation of Ceftiofur sodium by the condensation of 3-[2-(furylcarbonyl)thiomethyl]-3-cephem-4-carboxylic acid as represented by formula (II) with 5-phenyl-1,3,4-oxadiazole-2-thio-2-(2-aminothiazol-4-yl)2-methoxyimino) acetate as represented by formula (III) and the Ceftiofur amine salt thus obtained is converted into its sodium salt.

BACKGROUND OF INVENTION

Ceftiofur is a generic name given to the compound of formula (Ia)

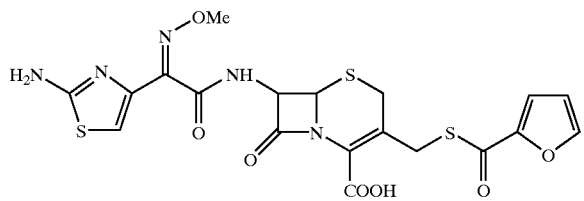

(Ia)

Ceftiofur acid, its alkali metal, alkaline earth metal and amines salts were reported for the first time in U.S. Pat. No. 4,464,367. During the course of further investigation, later on, it was discovered that all these derivatives of Ceftiofur are known to have stability problems. Further, it was difficult to purify the derivative of Ceftiofur due to amorphous nature of the compound. In fact, from the beginning, preparation of Ceftiofur sodium has posed challenges to organic chemists regarding purity, stability and crystallinity.

Several attempts have been made to prepare Ceftiofur sodium for obviating above-mentioned problems. One of the solutions was provided in U.S. Pat. No. 4,877,782 by preparing zinc complexes of Ceftiofur which have better dispersibility in water and can be used in pharmacological preparations. U.S. Pat. No. 4,902,683 also explains the isolation of more stable Ceftiofur in the form of crystalline hydrohalide salts which has better solubility and other physical properties, as compared to parent compounds. During the isolation of Ceftiofur hydrochloride salt most of the impurities present in the compound are removed during filtration. The hydrohalide salts as such cannot be used for parenteral administration, therefore it is necessary to convert a hydrohalide salt to sodium salt in order to use the drug as injectable.

Several methods are reported in chemical literature for converting cephalosporanic acids to their corresponding alkali metal salts. This step is of special importance in case of injectable antibiotics. Surprisingly, very few methods are disclosed for preparing Ceftiofur sodium starting from either Ceftiofur hydrohalide salt or Ceftiofur acid. Using conventional method, it is extremely difficult to get pure Ceftiofur sodium from Ceftiofur hydrochloride without isolating Ceftiofur acid as intermediate. During the neutralization of Ceftiofur hydrochloride with any sodium base, one molecule of hydrochloric acid attached to Ceftiofur also get neutralized resulting in the formation of sodium chloride which is very difficult to remove from the required compound. Till date, there is no chemical method reported to separate the sodium chloride from Ceftiofur sodium since both have very similar properties, especially, solubility. Alternatively, one can isolate Ceftiofur acid first and then treat it with sodium base but it is also problematic due to its amorphous nature of Ceftiofur acid and severe problems during filtration of Ceftiofur acid are also encountered.

U.S. Pat. No. 4,937,330 describes the use of polyvinylpyridine for neutralization of hydrohalide salt to get free acid and then treating the free acid, in situ with sodium-2-ethylhexanoate. The use of sodium-2-ethyl hexanoate for this purpose is subject of several patents in field of cephalosporin antibiotics. The polyvinyl pyridine resin loses activity after certain batches and needs replacement, which makes the process expensive.

In general, the process for liberation of Ceftiofur free acid from hydrohalide salt using either resin bases or non-resin bases is associated with above problems. Keeping all these problems in mind, the applicant disclose a simple, economical and commercially viable process for preparing Ceftiofur sodium which obviates all the above mentioned limitations. In this regard, a reference to applicants co-pending U.S. patent application Ser. No. 09/754,302 is also made herewith.

OBJECTS OF THE INVENTION

Therefore, the primary object of the invention is to provide a process for preparing Ceftiofur sodium without the preparation of Ceftiofur hydrochloride as an intermediate.

Another object of the invention is to concentrate the aqueous solution of Ceftiofur amine salt as well as Ceftiofur sodium salt by employing evaporation under reduced pressure using effective heat transfer methods.

Yet another object of this invention is to prevent the deterioration of product during evaporation process.

Still another object of the invention is to prepare Ceftiofur Sodium from Ceftiofur amine by treating with sodium-2-ethylhexanote, sodium acetate, sodium-bi-carbonate or sodium lactate.

One more object of the invention is to precipitate Ceftiofur sodium using an organic solvent.

Further object of the present invention is to prepare buffered Ceftiofur sodium from Ceftiofur amine salt.

Still another object of the invention is to provide Ceftiofur sodium from Ceftiofur amine salt solution by neutralizing the Ceftiofur amine salt solution with stoichiometric equivalent of mineral acid in presence of sodium chloride and organic solvent, followed by treating the organic layer with sodium base.

SUMMARY OF THE INVENTION

To meet the above objectives, the present invention provides a process for the preparation of Ceftiofur sodium by the condensation of 3-[2-(furylcarbonyl)thiomethyl]-3-cephem-4-carboxylic acid with 5-phenyl-1,3,4-oxadiazole-2-thio-2-(2-aminothiazol-4-yl)2-methoxyimino)acetate. The Ceftiofur amine salt obtained during the condensation is converted in situ into its sodium salt. The solution thus obtained is concentrated without subjecting to high temperature by using highly efficient evaporation techniques which hitherto not been used for this class of compounds. The Ceftiofur amine salt is converted into its sodium salt by using sodium-2-ethylhexanoate, sodium acetate or sodium bicarbonate. Finally, Ceftiofur sodium can be isolated by crystallizing out by the addition of an organic solvent.

DETAILED DESCRIPTION OF THE INVENTION

The present invention provides a process for the preparation of Ceftiofur sodium (I),

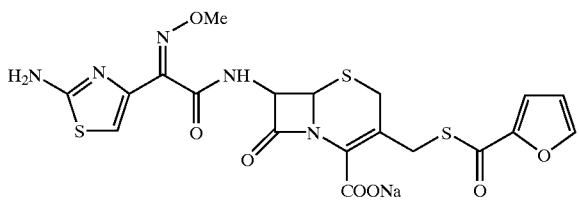

the said process comprising the steps of:

(a) condensing 3-[2-(furylcarbonyl)thiomethyl]-3-cephem-4-carboxylic acid represented by formula (II) with 5-phenyl-1,3,4-oxadiazole-2-thio-2-(2-aminothiazol-4-yl)2-methoxyimino)acetate represent by formula (III) in a mixture of water and an organic solvent, in the presence of an amine base, at a pH range of 7.0 to 8.5 and at a temperature between −25° C. and 30° C. and

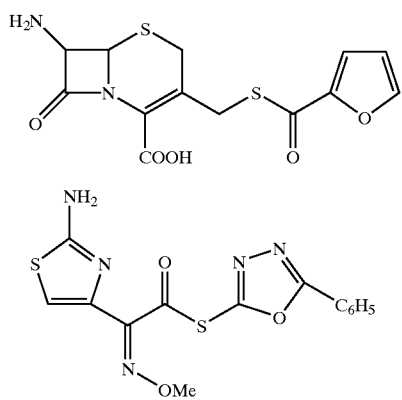

subsequent extraction with a solvent selected from dichloromethane or ethylacetate to get Ceftiofur amine salt which is isolated in the aqueous phase, (b) treating the aqueous solution of Ceftiofur amine salt of step(a) with charcoal, filtering and evaporating the aqueous solution by employing a highly efficient evaporation technique under vacuum to remove water to yield a slurry of Ceftiofur amine salt, (c) treating the slurry of step (b) containing Ceftiofur amine salt with sodium base and precipitating and isolating Ceftiofur sodium by adding organic solvent, followed by filtering the precipitated solid and drying the filtered solid, and (d) treating Ceftiofur sodium of step (c) with a potassium dihydrogen phosphate buffer at pH 7.5, followed by sterile filtration using micron filter and lyophilisation to get sterile buffer Ceftiofur sodium.

A process wherein Ceftiofur sodium is obtained alternatively by adding an organic solvent to Ceftiofur amine salt solution, the mixture is neutralized with stoichiometric amount of mineral acid and sodium chloride is added in order to separate organic layer which is treated with charcoal, filtered and treated with a sodium base to precipitate Ceftiofur sodium which is filtered, dried and treating it with potassium dihydrogen phosphate buffer at pH 7.5, followed by sterile filtration using micron filter and lyophilisation to get sterile buffer Ceftiofur sodium.

In the above process, the condensation reaction of step (a) is quenched by adding dichloromethane or ethylacetate into the reaction mixture. Addition of dichloromethane or ethyl acetate removes all the impurities, which are soluble in the organic phase. The organic phase is separated from aqueous phase that contains Ceftiofur amine salt. The concentration of Ceftiofur amine salt in aqueous solution is about 10–15%. It is difficult to isolate Ceftiofur sodium by adding any amount of organic solvent at this concentration. The aqueous solution containing Ceftiofur as amine salt is treated with two different methods to achieve maximum yield and purity of the product. The aqueous layer isolated from the reaction is treated by two different routes described hereinbelow.

The aqueous solution separated from reaction has about 10–15% concentration of Ceftiofur amine salt in water. In order to reduce the amount of water from this solution, it is subjected to the distillation of water. Since, the stabilities of cephalosporins are not very good in solution at high temperature, only a technique, which could remove water at very fast rate and without heating the product at higher temperature, can be useful for the purpose.

After studying several evaporating and drying processes, the Applicants feel that film evaporators and drier are best suited for the present process. Attempts to concentrate this solution from initial low concentration by batch distillation under reduced pressure causes very high degree of decomposition as product is exposed to heat due to large residence time. Using low temperature distillation technique known as film evaporation can carry out the removal of such a large amount of water. Agitated thin film evaporator, falling film evaporator, rising film evaporator, forced circulation evaporator etc are few devices, which work on this principle. Thin film evaporation is a continuous distillation process and has never been reported for isolation of Ceftiofur salts by anybody. The total residence time of compound in evaporator is of few seconds. This avoids exposure of product for long time to high temperature. Hence, reducing the decomposition of product. The dilute solution is fed to agitated thin film evaporator having a high-speed rotor. Feed is spread as a thin film. Water is evaporated immediately as there is a large differential temperature across the unit. The entire unit is kept at reduced pressure of the order of 10 to 20 mm of Hg. Use of this technique avoids heating the compound for longer duration, which prevents decomposition of product during evaporation.

Highly concentrated thick slurry of Ceftiofur amine salt is isolated and treated with sodium-2-ethylhexanoate or sodium acetate or sodium bicarbonate or sodium lactate. The thick slurry containing Ceftiofur sodium is slowly poured into a pool of an organic solvent which precipitates out white to creamish solid. The solid thus obtained is filtered under nitrogen atmosphere. The success of this process lies in the ability of evaporators to concentrate the Ceftiofur salt solution in minimum time and at temperature at which decomposition is negligible. Alternatively, the same set of operation is also done by first converting Ceftiofur amine salt to sodium salt and then evaporation of water using above-mentioned technique.

Alternatively, an organic solvent is added to the aqueous layer separated from the reaction. A stoichiometric amount of acid is added to neutralize the amine salt to make the carboxylate group free. As soon as the Ceftiofur amine salt is neutralized the partition coefficient shifted in favor of organic phase and Ceftiofur becomes soluble in the organic solvent. The two phases are separated, the organic phase is treated with sodium-2-ethylhexanoate or sodium acetate or sodium lactate at a temperature 0–20° C. Addition of more organic solvent into this results in thick precipitation of Ceftiofur sodium.

Both these routes provide methods by which Ceftiofur sodium can be obtained in high purity (95–99%) with excellent yield (85–95%) and at the same time, without the necessity for preparing Ceftiofur hydrochloride.

In an embodiment, the organic solvent used for carrying out the condensation of cephalosporin derivative of formula (II) and 2-amino-thiazol-4-yl-methoxyimino acetic acid derivative of (III) is selected from the group comprising tetrahydrofuran, 1,4-dioxane, ethylacetate, acetone, N,N-dimethylformamide, dichloromethane, methanol, acetonitrile and a mixture thereof.

In another embodiment, the amine base is selected from a group comprising triethylamine, diethylamine, diisopropylethylamine N-methylaniline or amines of similar structures but the preferred base is triethylamine.

In an embodiment, the organic solvent added for precipitating out Ceftiofur sodium from a aqueous solution is selected from the group comprising acetone, isopropyl alcohol, tetrahydrofuran, ethylacetate, 1,4-dioxane, acetonitrile and a mixture thereof.

In another embodiment, the concentration of aqueous solutions of Ceftiofur amine salt or Ceftiofur sodium salt is achieved by evaporating water with film evaporator at low temperatures about 10–35° C. and reduced pressure at 10–20 mm of Hg. The residence time of a few seconds with a narrow spread is an important feature when working with heat sensitive compounds. The evaporation is achieved in a single pass avoiding product re-circulation and possible degradation. The deposition of the product on the heat transfer surface is avoided due to the intense agitation in the liquid film. The evaporator is selected from agitated thin film evaporator, falling film evaporator, rising film evaporator or a combination thereof.

In yet another embodiment, the sodium base is selected from group of sodium-2-ethlyhexanoate, sodium bicarbonate, sodium lactate or sodium acetate.

In still another embodiment, the sterile buffered Ceftiofur sodium is obtained by treating Ceftiofur sodium with potassium dihydrogen phosphate buffer at a pH 7.5, followed by lyophilisation.

The invention is illustrated with the following examples, which should not be construed as limiting the scope of the invention.

EXAMPLE I

Sodium 7-[[(Z)-2-(aminothiazol-4-yl)-2-methoxyimino]acetamido]-3-(2-furanylcarbonyl)thiomethyl-3-cephem-4-carboxylate (sterile buffered Ceftiofur sodium)

7-amino-3-[(2-furanylcarbonyl)thiomethyl]-3-cephem-4-carboxylic acid (10.0 g) and 2-mercapto-5-phenyl-1,3,4-oxadiazolyl-(Z)-2-(2-aminothiazol-4-yl)-2-methoxyimino acetate (15.9 g) are added to a mixture of tetrahydrofuran (100 ml) and water (100 ml) at temperature 0–5° C. The pH of reaction is maintained at 7.0 to 8.0 by addition of triethylamine during the reaction. After completion of reaction, the reaction mixture is extracted with methylene chloride (100 ml×3). The aqueous layer is treated with charcoal (0.500 g). The filtrate is subjected to an agitated thin film evaporator working at 20° C.–25° C. with 15–20 mm of Hg, to obtain viscous slurry of Ceftiofur triethylamine salt. Sodium-2-ethylhexanoate (5.9 g) is added to the mass and the mixture is stirred vigorously. The homogeneous mixture is added slowly in the pool of isopropyl alcohol at a temperature of 20–25° C., white to creamish solid precipitated out in the solution, which is cooled to 0–5° C. for 2.0 h. Ceftiofur sodium thus prepared is filtered under inert atmosphere and dried under vacuum to obtain 13.0 g of Ceftiofur sodium. The Ceftiofur sodium thus prepared is dissolved in 120 ml of water. The pH of the solution is adjusted to 7.5 by adding sodium bicarbonate. Potassium dihydrogen phosphate (0.4–0.5 g) is added, the solution is filtered through a 0.2 micron filter under sterile condition and subjected to lyophilisation to obtain sterile buffered Ceftiofur sodium (13.4 g) with 97–98% HPLC purity.

EXAMPLE II

Sodium 7-[[(Z-2-(aminothiazol-4-yl)-2-methoxyimino]acetamido]-3-(2-furanylcarbonyl)thiomethyl-3-cephem-4-carboxylate (sterile buffered Ceftiofur sodium)

7-amino-3-[(2-furanylcarbonyl)thiomethyl]-3-cephem-4-carboxylic acid (5.0 g) and 2-mercapto-5-phenyl-1,3,4-oxadiazolyl-(Z)-2-(2-aminothiazol-4-yl)-2-methoxyimino acetate (7.59 g) are added to a mixture of acetone (50 ml) and water (50 ml) at temperature 0–5° C. The pH of reaction is maintained at 7.0 to 8.0 by addition of triethylamine during the reaction. After completion of reaction, the reaction mixture is extracted with methylene chloride (75 ml×3). The aqueous layer is treated with charcoal (0.250 g) and diluted with water. The filtrate is subjected to an agitated thin film evaporator working at 20° C.–25° C. with 15–20 mm of Hg, to get viscous slurry of Ceftiofur triethylamine salt. Sodium-2-ethylhexanoate (2.95 g) is added to the mass and the mixture is stirred vigorously. The homogeneous mixture is added slowly in 200 ml of acetone at a temperature of 20–25° C., white to creamish solid precipitated out in the solution, which is cooled to 0–5° C. for 2.0 h. Ceftiofur sodium thus prepared is filtered under inert atmosphere and dried under vacuum. Product is converted into buffered sterile Ceftiofur sodium as described in Example-I to get 14.0 g of Ceftiofur sodium with HPLC (purity) of 98.0%.

EXAMPLE III

Sodium 7-[[(Z)-2-(aminothiazol-4-yl)-2-methoxyimino]acetamido]-3-(2-furanylcarbonyl)thiomethyl-3-cephem-4-carboxylate (sterile buffered Ceftiofur sodium)

7-amino-3-[(2-furanylcarbonyl)thiomethyl]-3-cephem-4-carboxylic acid (5.0 g) and 2-mercapto-5-phenyl-1,3,4-oxadiazolyl-(Z)-2-(2-aminothiazol-4-yl)-2-methoxyimino acetate (7.59 g) are added to a mixture of acetone (50 ml) and water (50 ml) at temperature 0–5° C. The pH of reaction is maintained at 7.0 to 8.0 by addition of triethylamine during the reaction. After completion of reaction, the reaction mixture is extracted with methylene chloride (75 ml×3). The aqueous layer is treated with charcoal (0.250 g). The filtrate is treated with sodium bicarbonate (1.5 grams) and the resulting solution is subjected to an agitated thin film evaporator working at 20° C.–25° C. with 15–20 mm of Hg, to get viscous slurry. This slurry is added slowly to the pool of acetone at a temperature of 20–25° C., white to creamish solid precipitated out in the solution, which is cooled to 0–5° C. for 2.0 h. Ceftiofur sodium thus prepared is filtered under inert atmosphere and dried under vacuum. Product is converted into buffered sterile Ceftiofur sodium as describe in Example-I to obtain 14.0 g of Ceftiofur sodium with HPLC (purity) of 98.0%.

EXAMPLE IV

Sodium 7-[[(Z)-2-(aminothiazol-4-yl)-2-methoxyimino]acetamido]-3-(2-furanylcarbonyl)thiomethyl-3-cephem-4-carboxylate (sterile buffered Ceftiofur sodium)

7-Amino-3-[(2-furanylcarbonyl)thiomethyl]-3-cephem-4-carboxylic acid (30.0 g, 88.2 mmol) and 2-mercapto-5-phenyl-1,3,4-oxadiazolyl-(Z)-2-(2-aminothiazol-4-yl)-2-methoxyimino acetate (47.7 g, 132.0 mmol) are added to a mixture of dichloromethane (400 ml) and methanol (15 ml) at temperature 0–5° C. Triethylamine (25.0 ml) is added to the reaction mixture in 50–60 min. After completion of reaction, the reaction mixture is extracted with water (400 ml). The aqueous layer is separated and treated with charcoal (0.500 g). Tetrahydrofuran (400 ml) and 100 g of sodium chloride is added to this solution followed by addition of (9.2 ml) of hydrochloric acid (35%). The mixture is stirred for 10 min and layers are separated. Tetrahydrofuran layer is treated with charcoal and 75 ml solution tetrahydrofuran containing 13.5 g of sodium-2-ethylhexanoate is added to tetrahydrofuran layer under stirring. Further, tetrahydrofuran (500 ml) is added to this mixture, solid precipitated out in the solution, which is cooled to 0–5° C. for 1.0–2.0 h. Ceftiofur sodium thus prepared is filtered under inert atmosphere, washed with acetone and dried under vacuum to get 36–38 g of Ceftiofur sodium with HPLC (purity) of 98.0%. The Ceftiofur sodium thus prepared is dissolved in 350 ml of water. The pH of the solution is adjusted to 7.5 by adding sodium bicarbonate. Potassium dihydrogen phosphate (1.44–1.6 g) is added, the solution is filtered through a 0.2 micron filter under sterile condition and subjected to lyophilisation to obtain sterile buffered Ceftiofur sodium (37–38 g).

EXAMPLE V

Sodium 7-[[(Z)-2-(aminothiazol-4-yl)-2-methoxyimino]acetamido]-3-(2-furanylcarbonyl)thiomethyl-3-cephem-4-carboxylate (sterile buffered Ceftiofur sodium)

7-amino-3-[(2-furanylcarbonyl)thiomethyl]-3-cephem-4-carboxylic acid (5.0 g) and 2-mercapto-5-phenyl-1,3,4-oxadiazolyl-(Z)-2-(2-aminothiazol-4-yl)-2-methoxyimino acetate (7.59 g) are added to a mixture of acetone (50 ml) and water (50 ml) at temperature 0–5° C. The pH of reaction is maintained at 7.0 to 8.0 by addition of triethylamine during the reaction. After completion of reaction, the reaction mixture is extracted with methylene chloride (75 ml×3). The aqueous layer is treated with sodium-2-ethylhexanoate (2.95 g) and charcoalized with activated charcoal (0.5 g). Charcoal is filtered and the filtrate is subjected to agitated thin film evaporator working at 20° C.–25° C. with 15–20 mm of Hg, to get viscous slurry of Ceftiofur sodium salt which is added is added slowly in 200 ml of acetone at a temperature of 20–25° C., white to creamish solid precipitated out in the solution, which is cooled to 0–5° C. for 2.0 h. Ceftiofur sodium thus prepared is filtered under inert atmosphere and dried under vacuum. Product is converted into buffered sterile Ceftiofur sodium as describe in Example-I to obtain 14.0 g of Ceftiofur sodium with HPLC (purity) of 98.0%.

What is claimed is:

1. A process for preparing Ceftiofur sodium of formula (I)

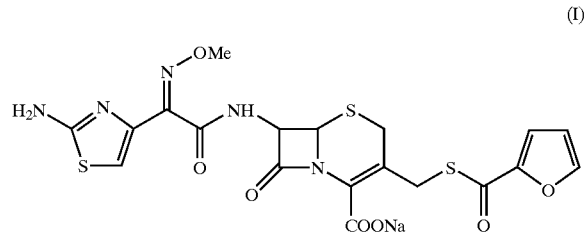

(I)

said process comprising the steps of:
(a) condensing 3-[2-(furylcarbonyl)thiomethyl]-3-cephem-4-carboxylic acid represented by formula (II) with 5-phenyl-1,3,4-oxadiazole-2-thio-2-(2-aminothiazol-4-yl)2-methoxyimino)acetate represented by formula (III) in a mixture of water and an organic solvent, in the presence of an amine base at a pH range of 7.0 to 8.5

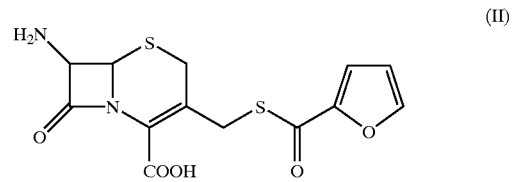

(II)

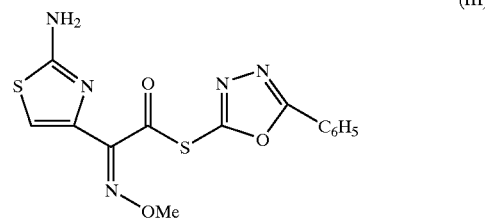

(III)

an at a temperature between −25° C. and 30° C. and subsequent extraction with a solvent selected from dichloromethane or ethylacetate, to obtain Ceftiofur amine salt in aqueous phase,
(b) treating the aqueous solution of Ceftiofur amine salt of step (a) with charcoal, filtering and evaporating the aqueous solution by employing an evaporation technique under vacuum to remove water to yield a slurry of Ceftiofur amine salt, and (c) treating the slurry of step (b) containing Ceftiofur amine salt with sodium base and precipitating and isolating Ceftiofur sodium by adding organic solvent, followed by filtering the precipitated solid and drying the filtered solid.

2. A process for preparing Ceftiofur sodium of formula (I)

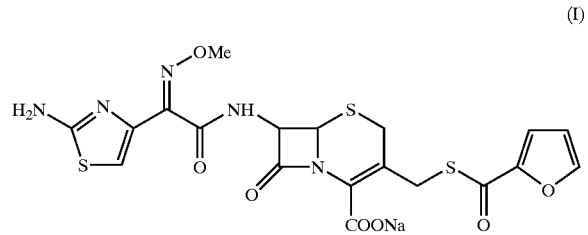

(I)

said process comprising the steps of:
(a) condensing 3-[2-(furylcarbonyl)thiomethyl]-3-cephem-4-carboxylic acid represented by formula (II)

with 5-phenyl-1,3,4-oxadiazole-2-thio-2-(2-aminothiazol-4-yl)-2-methoxyimino)acetate represented by formula (III) in a mixture of water and an organic solvent, in the presence of an amine base at a pH range of 7.0 to 8.5

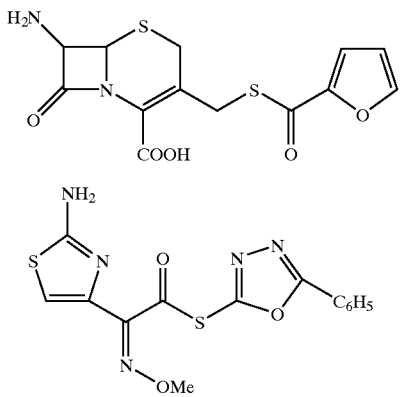

and at a temperature between −25° C. and 30° C. and subsequent extraction with a solvent selected from dichloromethane or ethylacetate to obtain Ceftiofur amine salt in aqueous phase;
(b) adding an organic solvent to the aqueous solution of Ceftiofur amine salt of step (a) and neutralizing the mixture with a stoichiometric amount of a mineral acid; and
(c) adding sodium chloride to separate an organic layer which is treated with charcoal, filtered and treated with a sodium base to precipitate Ceftiofur sodium followed by filtering the precipitated solid and drying the filtered solid.

3. A process as claimed in claim 1, wherein in step (a) the organic solvent is selected from a group comprising tetrahydrofuran, N,N-dimethyl formamide, 1,4-dioxane, acetone, ethylacetate, dichloromethane, methanol, acetonitrile or mixture thereof.

4. A process as claimed in claim 1, wherein in step (a) the amine base is selected from a group comprising triethylamine, diethylamine, diisopropylethylamine, N-methylaniline or mixtures thereof.

5. A process as claimed in claim 1, wherein in step (b) the Ceftiofur amine salt solution is evaporated by employing a rising film evaporator, falling film evaporator, agitated thin film evaporator, forced circulation evaporator or combination thereof.

6. A process as claimed in claim 1, wherein in step (b) the evaporation is performed at a temperature of about 10–35° C. and at a reduced pressure of 10–20 mm of mercury.

7. A process as claimed in claim 1, wherein in step (b) the evaporation is achieved in single pass avoiding product re-circulation and possible degradation.

8. A process as claimed in claim 1, wherein in step (b) the deposition of product on a heat transfer surface during evaporation is avoided by intense agitation of the aqueous solution.

9. A process as claimed in claim 1, wherein in step (c) the sodium base is selected from a group comprising sodium lactate, sodium-2-ethyl hexanoate, sodium acetate or sodium bicarbonate.

10. A process as claimed in claim 2, wherein the sodium base is selected from a group comprising sodium lactate, sodium-2-ethylhexaonate, sodium acetate or sodium bicarbonate.

11. A process as claimed in claim 2, wherein the neutralization of Ceftiofur amine salt is carried out by using one mole equivalent of hydrohalic acid.

12. A process as claimed in claim 2, wherein the Ceftiofur amine salt solution is added to an organic solvent selected from a group comprising tetrahydrofuran, acetone, isopropyl alcohol, acetonitrile or 1,4-dioxane.

13. A process as claimed in claim 1, wherein in step (c) the Ceftiofur sodium is precipitated by an organic solvent selected from a group comprising tetrahydrofuran, acetone, ethylacetate, isopropyl alcohol, acetonitrile, 1,4-dioxane or mixtures thereof.

14. A process as claimed in claim 2, wherein the Ceftiofur sodium is precipitated by an organic solvent selected from a group comprising tetrahydrofuran, acetone, ethylacetate, isopropyl alcohol, 1,4-dioxane, acetonitrile or mixtures thereof.

15. A process as claimed in claim 1, wherein the amine base in step (a) is triethylamine.

16. A process as claimed in claim 1, wherein the sodium base in step (c) is sodium-2-ethyl hexanoate.

17. A process as claimed in claim 2, wherein the sodium base in step (c) is sodium-2-ethyl hexanoate.

18. A process as claimed in claim 11, wherein the neutralization of Ceftiofur amine salt is carried out by using one mole equivalent of hydrochloric acid.

19. A process as claimed in claim 12, wherein the organic solvent is tetrahydrofuran.

20. A process as claimed in claim 1, wherein the precipitation of Ceftiofur sodium is obtained by adding an organic solvent.

21. A process according to claim 2, further comprising treating Ceftiofur sodium of step (c) with a potassium dihydrogen phosphate buffer at pH 7.5, followed by sterile filtration using micron filter and lyophilisation to get sterile buffered Ceftiofur sodium.

22. A process according to claim 1, further comprising treating Ceftiofur sodium of step (c) with a potassium dihydrogen phosphate buffer at pH 7.5, followed by sterile filtration using micron filter and lyophilisation to obtain a sterile buffered Ceftiofur sodium.

* * * * *